(12) United States Patent
Furukawa et al.

(10) Patent No.: US 10,973,392 B2
(45) Date of Patent: Apr. 13, 2021

(54) ADHESIVE FOR ENDOSCOPE, CURED PRODUCT, ENDOSCOPE, AND METHOD FOR PRODUCING ENDOSCOPE

(71) Applicant: FUJIFILM Corporation, Tokyo (JP)

(72) Inventors: Kazushi Furukawa, Kanagawa (JP); Toshihide Yoshitani, Kanagawa (JP); Yoshihiro Nakai, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/802,130

(22) Filed: Feb. 26, 2020

(65) Prior Publication Data

US 2020/0187755 A1 Jun. 18, 2020

Related U.S. Application Data

(63) Continuation of application No. PCT/JP2018/031543, filed on Aug. 27, 2018.

(30) Foreign Application Priority Data

Aug. 30, 2017 (JP) .............................. JP2017-165918

(51) Int. Cl.
*A61B 1/00* (2006.01)
*C09J 163/00* (2006.01)

(52) U.S. Cl.
CPC ...... *A61B 1/00064* (2013.01); *A61B 1/00128* (2013.01); *C09J 163/00* (2013.01)

(58) Field of Classification Search
CPC .... C08L 63/00; C09J 163/00; C08G 59/4014; A61B 1/00
See application file for complete search history.

(56) References Cited

U.S. PATENT DOCUMENTS

| | | | |
|---|---|---|---|
| 3,632,795 A * | 1/1972 | Thomas | C08L 63/00 528/114 |
| 4,214,067 A * | 7/1980 | Packer | C08G 59/66 528/93 |
| 2007/0129466 A1 | 6/2007 | Kagawa et al. | |
| 2015/0240137 A1 | 8/2015 | Yokoyama et al. | |
| 2020/0190252 A1 | 6/2020 | Voci et al. | |

FOREIGN PATENT DOCUMENTS

| | | |
|---|---|---|
| EP | 2 172 518 A1 | 4/2010 |
| JP | H11-060694 A | 3/1999 |
| JP | 2002-238834 A | 8/2002 |
| JP | 2011-026457 A | 2/2011 |
| WO | 2006/013860 A1 | 2/2006 |
| WO | 2018/219961 A1 | 12/2018 |

OTHER PUBLICATIONS

International Search Report issued in PCT/JP2018/031543; dated Sep. 18, 2018.
International Preliminary Report on Patentability issued in PCT/JP2018/031543; completed Aug. 2, 2019.
The extended European search report issued by the European Patent Office dated Sep. 11, 2020, which corresponds to European Patent Application No. 18851971.4-1107 and is related to U.S. Appl. No. 16/802,130.

\* cited by examiner

*Primary Examiner* — Kuo Liang Peng
(74) *Attorney, Agent, or Firm* — Studebaker & Brackett PC

(57) ABSTRACT

Provided are an adhesive for an endoscope, a cured product, an endoscope, and a method for producing an endoscope. The adhesive for an endoscope is a two-component adhesive for an endoscope. The two-component adhesive has a base and a curing agent. The base includes at least one epoxy resin (A) selected from the group consisting of bisphenol A epoxy resins, bisphenol F epoxy resins, and phenol novolac epoxy resins. The curing agent includes a tertiary amine compound (B). The tertiary amine compound (B) accounts for 60 mass % or more of a curing component included in the curing agent.

6 Claims, 3 Drawing Sheets

ADHESIVE FOR ENDOSCOPE, CURED PRODUCT, ENDOSCOPE, AND METHOD FOR PRODUCING ENDOSCOPE

CROSS-REFERENCE TO RELATED APPLICATIONS

This application is a Continuation of PCT International Application No. PCT/JP2018/031543 filed on Aug. 27, 2018, which claims priority under 35 U.S.C. § 119 (a) to Japanese Patent Application No. 2017-165918 filed in Japan on Aug. 30, 2017. Each of the above applications is hereby expressly incorporated by reference, in its entirety, into the present application.

BACKGROUND OF THE INVENTION

1. Field of the Invention

The present invention relates to an adhesive for an endoscope, a cured product, an endoscope, and a method for producing an endoscope.

2. Description of the Related Art

Endoscopes for examining human body cavities are repeatedly used. Thus, a flexible tube constituting an insertion section of an endoscope needs to be washed and disinfected with chemicals after each use.

In particular, when an endoscope is inserted into a highly susceptible region, such as a bronchus, high cleanliness at the level of sterilization higher than disinfection is required. Accordingly, the use of not only ethylene oxide gas (EOG) sterilization treatment, which is widely practiced, but also treatments having higher sterilization effects (e.g., hydrogen peroxide plasma treatment) has been demanded.

The insertion section of an endoscope is inserted into a body cavity through the oral cavity or nasal cavity. To alleviate foreign body sensation and pain in patients during the insertion, the insertion section of an endoscope desirably has a smaller diameter. Thus, instead of bulky members such as screws, adhesives are mainly used to bond together members constituting the insertion section.

Among the adhesives, epoxy adhesives are used in various fields because they have high workability and cured products thereof are excellent in adhesiveness, electrical properties, heat resistance, moisture resistance, and other properties. There are also reports on techniques for improving the properties of epoxy adhesives. For example, JP2011-26457A discloses that an epoxy adhesive including a ketone solvent, a dicyandiamide powder serving as a curing agent, and an imidazole compound serving as a curing aid has high adhesive strength.

SUMMARY OF THE INVENTION

As described above, adhesives are used, for example, to fix constituent members of an endoscope. In general, however, a portion fixed or bonded using an adhesive tends to undergo degradation (e.g., decrease in adhesive strength) as a result of, for example, decomposition of a cured adhesive due to the above sterilization treatment, and the degradation of the adhesive joint causes a decrease in endoscope performance (e.g., optical performance and durability). JP2011-26457A describes a technique for improvement of an epoxy adhesive. However, JP2011-26457A does not describe the use of the adhesive for an endoscope. As a matter of course, no mention is made of disadvantages of using the adhesive in an endoscope.

Around an adhesive joint between, for example, a tip portion and an angle portion constituting an insertion section of an endoscope, a string is wound for reinforcement. The string is coated with an adhesive and surface finished. This helps insert the insertion section into a body cavity. For this purpose, it is required that the adhesive for an endoscope can be applied in a predetermined thickness, and in some cases, the thickness needs to be large, and suitability for thick coating is required.

An object of the present invention is to provide an adhesive for an endoscope and a cured product thereof. The adhesive is highly suitable for thick coating, is less likely to degrade and able to maintain sufficient adhesive strength when subjected to a sterilization treatment in the state of being used for fixation of a member, and is suitable for fixing a member constituting an endoscope. Another object of the present invention is to provide an endoscope that includes the cured product as a member for fixing a member constituting the endoscope and that is less likely to experience a decrease in performance when subjected to a sterilization treatment. Still another object of the present invention is to provide a method for producing the endoscope by using the adhesive for an endoscope.

The above objects have been achieved by the following means.

<1> A two-component adhesive for an endoscope has a base and a curing agent.

The base includes at least one epoxy resin (A) selected from the group consisting of bisphenol A epoxy resins, bisphenol F epoxy resins, and phenol novolac epoxy resins.

The curing agent includes a tertiary amine compound (B), and the tertiary amine compound (B) accounts for 60 mass % or more of a curing component included in the curing agent.

<2> In the adhesive for an endoscope according to <1>, the tertiary amine compound (B) includes a compound represented by general formula (I) below.

general formula (I)

In the formula. $R^1$ to $R^3$ each independently represent an aliphatic hydrocarbon group, an aromatic hydrocarbon group, or an aromatic heterocyclic group.

<3> The adhesive for an endoscope according to <1> or <2> is used in the form of a mixture of the base and the curing agent with the tertiary amine compound (B) being present in an amount of 0.5 to 10 parts by mass based on 100 parts by mass of the epoxy resin (A).

<4> A cured product is formed by curing the adhesive for an endoscope according to any one of <1> to <3>.

<5> An endoscope includes the cured product according to <4>. The cured product fixes at least one of a resin member, a metal member, or a glass member (a metal member and/or a glass member).

<6> A method for producing an endoscope includes fixing at least one of a resin member, a metal member, or a glass member by using the adhesive for an endoscope according to any one of <1> to <3>.

In the description of the present invention, the expression "to" is meant to include the numerical values before and after "to" as the lower and upper limits.

In the description of the present invention, when the number of carbon atoms of a group is specified, the number of carbon atoms means the number of carbon atoms of the whole group. That is, when the group further has a substituent, the number of carbon atoms means the number of carbon atoms of the whole including the substituent.

In the description of the present invention, substituents (as well as linking groups) not clearly specified as substituted or unsubstituted may have any substituent as long as the desired effects are produced. The same applies to compounds that are not specified as substituted or unsubstituted.

In the present invention, when there are a plurality of substituents, a plurality of linking groups, or the like represented by a particular symbol (hereinafter referred to as "substituents or the like") or when a plurality of substituents or the like are simultaneously or alternatively specified, the substituents or the like may be the same or different. Furthermore, even if not specifically stated, when a plurality of substituents or the like are adjacent to each other, they may be linked or fused to each other to form a ring.

The adhesive for an endoscope according to the present invention is highly suitable for thick coating, and is less likely to degrade and able to maintain high adhesiveness when subjected to a sterilization treatment in the state of being used for fixation of a member. Thus, the adhesive for an endoscope according to the present invention is suitable for fixing a member constituting an endoscope. The cured product according to the present invention is less likely to degrade when subjected to a sterilization treatment. Therefore, the endoscope according to the present invention, which has the cured product as a member for fixing a member constituting the endoscope, is also less likely to undergo degradation in performance when subjected to a sterilization treatment. According to the method for producing an endoscope according to the present invention, the above-described endoscope can be obtained.

DESCRIPTION OF THE PREFERRED EMBODIMENTS

Adhesive for Endoscope

Figure 1:
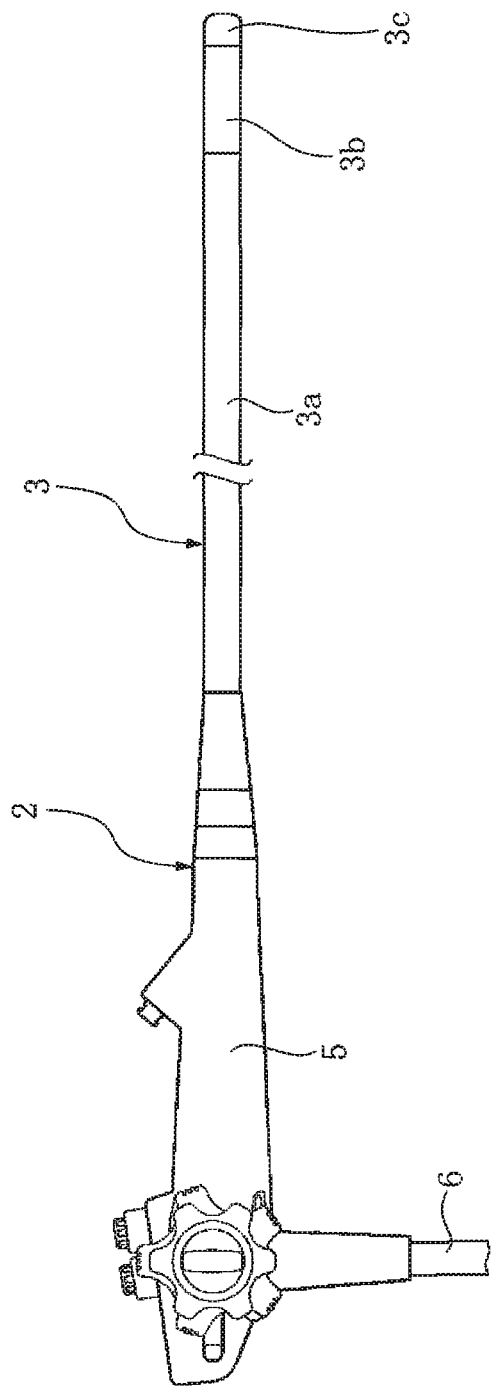
FIG. 1 is an external view illustrating a configuration of an endoscope according to an embodiment of the present invention.

An adhesive for an endoscope according to the present invention is a two-component adhesive that includes a base and a curing agent separate from each other (that is composed of a formulation including the base and a formulation including the curing agent).

The base includes at least one epoxy resin (A) selected from the group consisting of bisphenol A epoxy resins, bisphenol F epoxy resins, and phenol novolac epoxy resins. The curing agent includes a tertiary amine compound (B), and the tertiary amine compound (B) accounts for 60 mass % or more of a curing component (a component that acts on the epoxy resin to cure it) constituting the curing agent.

The adhesive for an endoscope according to the present invention is used to fix at least one of a resin member (the resin member includes a rubber member), a metal member, or a glass member constituting the endoscope. The "fixing" is performed by bonding at least one of the resin member, the metal member, or the glass member to, for example, a supporting member constituting the endoscope. The supporting member may be a tube wall or the like of the endoscope or an immovable member fixed to the tube wall or the like, or may be a member whose relative position in the endoscope can be moved like a tube. In the present invention, the term "fixing" is meant to include filling, that is, sealing, with a cured adhesive, a space between the above member and the supporting member incorporated with the above member.

Hereinafter, the "adhesive for an endoscope" may be referred to simply as the "adhesive". A fixing portion or a sealing portion formed of the above cured adhesive between a member and a member may be referred to as an adhesive joint.

The adhesive according to the present invention is highly suitable for thick coating. A cured product formed by curing the adhesive is less likely to undergo oxidization degradation when subjected to a powerful sterilization treatment such as hydrogen peroxide plasma sterilization treatment. Therefore, an endoscope produced using the adhesive according to the present invention is less likely to undergo performance degradation when repeatedly subjected to a sterilization treatment. Although not clear, the reasons for this are probably as follows.

The tertiary amine compound (B) constituting the curing agent is able, with a small amount (catalytic amount), to cure the epoxy resin (A). Thus, the amount of the curing agent used is small, and as a result, the viscosity of a mixture obtained by mixing the base with the curing agent can be maintained at a certain level, thus achieving a desired thick coating. A polymer obtained by opening the ring of the epoxy resin (A) with the tertiary amine compound (B) has an alkyleneoxy group as a repeating structure. That is, unlike polyamidoamines, the polymer does not have an amide bond, which is considered to react and decompose upon hydrogen peroxide plasma sterilization treatment, and provides a cured product with increased sterilization resistance.

Epoxy Resin (A)

The epoxy resin (A) used in the present invention includes at least one of a bisphenol A epoxy resin, a bisphenol F epoxy resin, or a phenol novolac epoxy resin. These epoxy resins may be used alone or may be used in combination.

The bisphenol A epoxy resin used in the present invention is not particularly limited and may be any bisphenol A epoxy resin commonly used as a base of an epoxy adhesive. Specific examples include bisphenol A diglycidyl ethers (e.g., "jER825", "jER828", and "jER834" (trade names) manufactured by Mitsubishi Chemical Corporation) and bisphenol A propoxylate diglycidyl ethers.

The bisphenol F epoxy resin used in the present invention is not particularly limited and may be any bisphenol F epoxy resin commonly used as a base of an epoxy adhesive. Specific examples include bisphenol F diglycidyl ethers (e.g., "EPICLON 830" (trade name) manufactured by DIC Corporation) and 4,4'-methylenebis(N,N-diglycidylaniline).

The phenol novolac epoxy resin used in the adhesive according to the present invention is not particularly limited and may be any phenol novolac epoxy resin commonly used as a base of an epoxy adhesive. Specific examples include product number 406775 manufactured by Sigma-Aldrich.

Tertiary Amine Compound (B)

The tertiary amine compound (B) used in the present invention may be any tertiary amine compound commonly used as a curing agent of an epoxy adhesive and preferably includes a compound represented by general formula (I) below. The percentage of the compound represented by general formula (I) below in the tertiary amine compound (B) is preferably 85 mass % or more, preferably 90 mass % or more, particularly preferably 95 mass % or more, and may be 100 mass %.

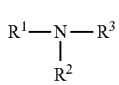

general formula (I)

In the formula, $R^1$ to $R^3$ each independently represent an aliphatic hydrocarbon group, an aromatic hydrocarbon group, or an aromatic heterocyclic group. At least two of $R^1$ to $R^3$ may be linked together to form a 5- to 7-membered ring or a fused ring of 5- to 7-membered rings.

The aliphatic hydrocarbon group may include, in its chain, one or more heteroatoms (preferably nitrogen atoms).

The aliphatic hydrocarbon group may be substituted with a substituent selected from the group consisting of substituents T described below. The substituent that may be present in the aliphatic hydrocarbon group may be, for example, an aryl group. The aryl group may further be substituted with a substituent T, and examples of aryl groups substituted with a substituent T include an aryl group substituted with an aminoalkyl group and an aryl group substituted with a hydroxy group.

The above ring that may be formed by at least two of $R^1$ to $R^3$ linking together may include a heteroatom (preferably a nitrogen atom) as an annular atom and may include an unsaturated bond as a bond constituting the ring.

The number of the above rings that may be formed by at least two of $R^1$ to $R^3$ linking together may be one or two or more. When two or more rings are formed, the compound represented by general formula (I) may have a bridged ring.

The compound represented by general formula (I) is preferably a compound represented by general formula (II) below.

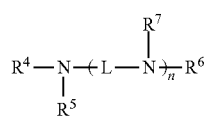

general formula (II)

In the formula, n represents an integer of 0 to 10. $R^4$ to $R^7$ each independently represent an alkyl group or an aryl group. L represents an alkylene group. At least two of $R^4$ to $R^7$ may be linked together to form a 5- to 7-membered ring or a fused ring of 5- to 7-membered rings, but these rings are preferably not formed.

n is preferably an integer of 0 to 6, more preferably an integer of 0 to 3.

The number of carbon atoms of the alkyl group is preferably 1 to 40, more preferably 1 to 20, particularly preferably 1 to 10. The alkyl group may be linear or branched, and examples include methyl, ethyl, propyl, isopropyl, butyl, t-butyl, and octyl.

The alkyl group may include, in its chain, one or more heteroatoms (preferably nitrogen atoms).

The alkyl group may be substituted with a substituent selected from the group consisting of substituents T described below. The substituent that may be present in the alkyl group may be, for example, an aryl group. The aryl group may further be substituted with a substituent T, and examples of aryl groups substituted with a substituent T include an aryl group substituted with an aminoalkyl group and an aryl group substituted with a hydroxy group.

The above ring that may be formed by at least two of $R^4$ to $R^7$ linking together may include a heteroatom (preferably a nitrogen atom) as an annular atom and may include an unsaturated bond as a bond constituting the ring.

The number of the above rings that may be formed by at least two of $R^4$ to $R^7$ linking together may be one or two or more. When two or more rings are formed, the compound represented by general formula (II) may have a bridged ring.

The number of carbon atoms constituting the ring of the aryl group is preferably 6 to 14, more preferably 6 to 10. Specific examples of the aryl group include phenyl and naphthyl.

The number of carbon atoms of the alkylene group is preferably 1 to 20, more preferably 1 to 15, particularly preferably 1 to 10. Specific examples of the alkylene group include methylene, ethylene, trimethylene, ethylethylene, and hexamethylene.

The tertiary amine compound (B) used in the present invention may have a substituent selected from the group consisting of substituents T below.

Examples of substituents T include the following.

Examples include alkyl groups (preferably having 1 to 20 carbon atoms), alkenyl groups (preferably having 2 to 20 carbon atoms), alkynyl groups (preferably having 2 to 20 carbon atoms), cycloalkyl groups (preferably having 3 to 20 carbon atoms, alkyl groups as used herein are generally meant to include cycloalkyl groups), aryl groups (preferably having 6 to 26 carbon atoms), aralkyl groups (preferably having 7 to 23 carbon atoms), heterocyclic groups (preferably heterocyclic groups having 2 to 20 carbon atoms, preferably 5- or 6-membered heterocyclic groups having at least one oxygen atom, sulfur atom, or nitrogen atom), alkoxy groups (preferably having 1 to 20 carbon atoms), aryloxy groups (preferably having 6 to 26 carbon atoms, alkoxy groups as used herein are generally meant to include aryloxy groups), alkoxycarbonyl groups (preferably having 2 to 20 carbon atoms), aryloxycarbonyl groups (preferably having 6 to 26 carbon atoms), amino groups (preferably amino groups having 0 to 20 carbon atoms, more preferably amino groups in which a nitrogen atom is substituted with an alkyl group or an aryl group (alkylamino groups, arylamino groups)), sulfamoyl groups (preferably having 0 to 20 carbon atoms), acyl groups (preferably having 1 to 20 carbon atoms), aryloyl groups (preferably having 7 to 23 carbon atoms, acyl groups as used herein are generally meant to include aryloyl groups), acyloxy groups (preferably having 1 to 20 carbon atoms), aryloyloxy groups (preferably having 7 to 23 carbon atoms, acyloxy groups as used herein are generally meant to include aryloyloxy groups), carbamoyl groups (preferably having 1 to 20 carbon atoms), acylamino groups (preferably having 1 to 20 carbon atoms), alkylthio groups (preferably having 1 to 20 carbon atoms), arylthio groups (preferably having 6 to 26 carbon atoms), alkylsulfonyl groups (preferably having 1 to 20 carbon atoms), arylsulfonyl groups (preferably having 6 to 22 carbon atoms), alkylsilyl groups (preferably having 1 to 20 carbon atoms), arylsilyl groups (preferably having 6 to 42 carbon atoms), alkoxysilyl groups (preferably having 1 to 20 carbon atoms), aryloxysilyl groups (preferably having 6 to 42 carbon atoms), phosphoryl groups (preferably phosphoryl groups having 0 to 20 carbon atoms, for example, —OP(=O)($R^P$)$_2$), phosphonyl groups (preferably phosphonyl groups having 0 to 20 carbon atoms, for example, —P(=O)($R^P$)$_2$), phosphinyl groups (preferably phosphinyl groups having 0 to 20 carbon atoms, for example, —P($R^P$)$_2$), (meth)acryloyl groups, (meth)acryloyloxy groups, (meth)acryloylimino groups ((meth)acrylamide groups), hydroxy groups, sulfanyl groups, carboxy groups, phosphate groups, phosphonate groups, sulfonate groups, cyano groups, and halogen atoms (e.g., fluorine, chlorine, bromine, and iodine). $R^P$ is a hydrogen atom, a hydroxy group, or a substituent (preferably a group selected from the group consisting of substituents T).

These groups listed as substituents T may be further substituted with any of the above substituents T.

When a compound, a substituent, a linking group, and the like include, for example, an alkyl group, an alkylene group, an alkenyl group, an alkenylene group, an alkynyl group, or an alkynylene group, these groups may be cyclic or chain-like, may be linear or branched, and may be substituted as described above or unsubstituted.

The molecular weight of the tertiary amine compound (B) is preferably, but not necessarily, 50 to 1000, more preferably 50 to 500, particularly preferably 100 to 400.

Examples of the tertiary amine compound (B) used in the present invention include, but are not limited to, the following.

Tributylamine, tri-n-octylamine, N,N-diisopropylethylamine, N,N,N'N'-tetramethylethylenedianline, N,N,N'N'-tetramethyl-1,3-diaminopropane, N,N,N'N'-tetramethyl-1,6-hexamethylenediamine, 1,1,4,7,10,10-hexamethyltriethylenetetramine, N-methylpiperidine, N-methylpyrrolidine. N,N'-dimethylpiperazine, 2,4,6-tris(dimethylaminomethyl)phenol, N-benzyldimethylamine, 1,8-diazabicyclo[5.4.0]-7-undecene, 1,4-diazabicyclo[2.2.2]octane, 2-(dimethylaminomethyl)phenol The adhesive according to the present invention is highly suitable for thick coating and is also highly suitable for injection or application into a minute portion. That is, the adhesive according to the present invention can be smoothly injected or applied into a minute portion of a constituent member of an endoscope.

This can be explained in part by the fact that when a chain-like tertiary amine compound (B) or a tertiary amine compound (B) having a non-aromatic ring is used, a mixture obtained by mixing the base with the curing agent can stay in a low-viscosity state for a while, and the mixture becomes more viscous (has thixotropic properties) immediately after coming to rest after injection or application.

This can also be explained in part by the fact that when a tertiary amine compound (B) having an aromatic ring is used, the compound interacts with the epoxy resin (A) constituting the base to thereby improve the anti-dripping properties at the time of adhesive application.

In the present invention, one single tertiary amine compound (B) may be used alone, or two or more tertiary amine compounds (B) may be used in combination.

The adhesive according to the present invention is preferably used in the form of a mixture of the base and the curing agent with the tertiary amine compound (B) constituting the curing agent being present in an amount of 0.5 parts by mass or more (more preferably 1 part by mass or more, still more preferably 2 parts by mass or more) based on 100 parts by mass of the epoxy resin (A) constituting the base. The adhesive is preferably used in the form of a mixture of the base and the curing agent with the tertiary amine compound (B) constituting the curing agent being present in an amount of 10 parts by mass or less (preferably 8 parts by mass or less, still more preferably 5 parts by mass or less) based on 100 parts by mass of the epoxy resin (A) constituting the base.

The content of the epoxy resin (A) in the base is preferably 80 mass % or more, more preferably 90 mass % or more, and may be 100 mass %. The base may include an epoxy resin other than the epoxy resin (A), a solvent, a plasticizer, an adhesion improver (e.g., a silane coupling agent), a surfactant, a colorant (e.g., a pigment, a dye), a weathering agent, an antioxidant, a heat stabilizer, a lubricant, an antistatic agent, a whitener, a release agent, a conductive agent, a viscosity regulator, a filler (e.g., silica, calcium carbonate), a thixotropy-imparting agent, a diluent (e.g., a monofunctional epoxy compound), and/or a flame retardant as long as the effects of the present invention are not impaired. The adhesive according to the present invention may be, for example, diluted with a diluent for use for injection or application into a minute portion.

In the present invention, the tertiary amine compound (B) functions as a curing agent of an epoxy adhesive. Thus, the tertiary amine compound (B) accounts for 60 mass % or more, preferably 70 mass % or more, more preferably 80 mass % or more, particularly preferably 90 mass % or more, of a curing component (a component that acts on the epoxy resin to cure it) in the curing agent. The tertiary amine compound (B) may account for all of the curing component in the curing agent. When the curing agent includes a curing component other than the tertiary amine compound (B), the curing component may be any curing agent or curing aid known as a curing component of an epoxy adhesive. For example, at least one of a primary amine compound, a secondary amine compound, an acid anhydride compound, an imidazole compound, a phosphorus compound, a thiol compound, a dicyandiamide compound, or a phenolic compound may be used in combination with the tertiary amine compound (B).

The curing agent may be composed of the above-described curing component or may include, in addition to the above-described curing component, a solvent, a filler, a plasticizer, a viscosity modifier, a diluent, and the like as long as the effects of the present invention are not impaired. The content of the curing component in the curing agent is preferably 80 mass % or more, more preferably 90 mass % or more.

Cured Product

A cured product according to the present invention is formed by curing the adhesive according to the present invention. That is, the cured product according to the present invention is used as a member constituting an adhesive joint of an endoscope. The cured product according to the present invention can be obtained by mixing the base and the curing agent of the adhesive according to the present invention and then curing the mixture, for example, by heating at 10° C. to 120° C. for 0.5 to 48 hours. The mixing of the base and the curing agent may be performed in the usual manner. The mixing is preferably performed while removing bubbles, and thus is usually performed under reduced pressure. If the above curing temperature is high, the endoscope will be exposed to high temperature for many times during the manufacturing process, and thus the curing temperature is preferably as low as possible. From this viewpoint, the curing temperature is preferably 100° C. or lower, more preferably 80° C. or lower. For the curing reaction to sufficiently proceed, the curing temperature is preferably 20° C. or higher, more preferably 40° C. or higher.

Endoscope

An endoscope according to the present invention has an adhesive joint between a fixed member and a resin member, a metal member, or a glass member, the adhesive joint being formed of the cured product according to the present invention.

An example of the endoscope (electronic endoscope) according to the present invention will be described. Electronic endoscopes are incorporated with a flexible tube for an endoscope (hereinafter a flexible tube for an endoscope may be referred to simply as a "flexible tube") and are widely used as medical instruments. In the example illustrated in FIG. 1, an electronic endoscope 2 includes an insertion section 3 to be inserted into a body cavity, a main-body operation section 5 connected to the proximal end portion of the insertion section 3, and a universal cord 6 to be connected to a processor device or a light source device. The insertion section 3 is composed of a flexible tube 3a connected to the main-body operation section 5, an angle portion 3b connected to the flexible tube 3a, and a tip portion 3c connected to the distal end of the angle portion 3b and mainly formed of a metal (e.g., stainless steel) member. An imaging device (not illustrated) for imaging a body cavity is built in the tip portion 3c. The flexible tube 3a, which occupies most of the length of the insertion section 3, is flexible over substantially the entire length thereof. In particular, a portion to be inserted into a body cavity or the like has a more flexible structure.

In FIG. 1, a plurality of channels (not illustrated) are formed that extend from the main-body operation section 5 to the distal end surface of the tip portion 3c through the insertion section 3 along the axis direction of the insertion section 3.

Figure 2:
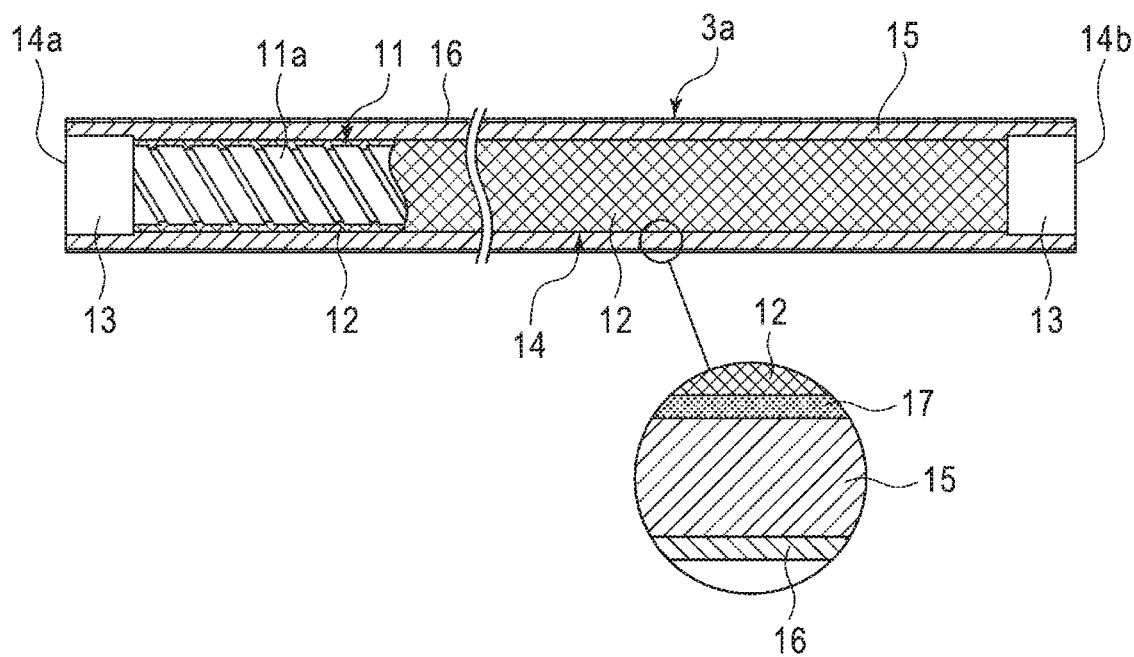
FIG. 2 is a partial sectional view illustrating a configuration of an insertion section of the endoscope illustrated in FIG. 1.

The flexible tube 3a in FIG. 1 is configured such that a resin layer 15 covers the outer peripheral surface of a flexible tube substrate 14, as illustrated in FIG. 2.

14a is the distal side (the tip portion 3c side), and 14b is the proximal side (the main-body operation section 5 side).

The flexible tube substrate 14 includes a spiral tube 11, which is disposed on the innermost side and formed by spirally winding a metal strip 11a, and a tubular net 12, which covers the spiral tube 11 and is formed by braiding metal wires. Caps 13 are fitted to opposite ends of the flexible tube substrate 14. The resin layer 15 is bonded to the flexible tube substrate 14 with a cured adhesive layer 17 interposed therebetween. While the cured adhesive layer (adhesive joint) 17 is illustrated as a layer having a uniform thickness for convenience of illustration, the cured adhesive layer 17 need not necessarily be in such a form and may be indeterminately interposed between the resin layer 15 and the flexible tube substrate 14. The cured adhesive layer 17 may rather have substantially no thickness such that the resin layer 15 and the flexible tube substrate 14 are substantially directly bonded together.

The outer surface of the resin layer 15 is coated with a coat layer 16 having chemical resistance and containing, for example, fluorine. To clearly illustrate the layer structure, the cured adhesive layer 17, the resin layer 15, and the coat layer 16 are illustrated as being thick relative to the diameter of the flexible tube substrate 14.

Figure 3:
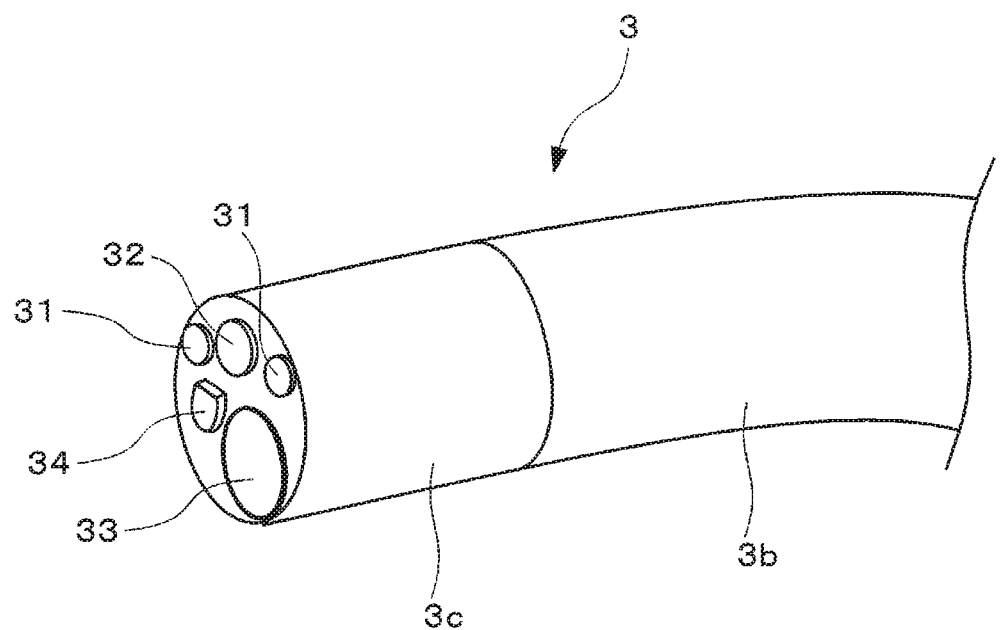
FIG. 3 is an external perspective view of a tip portion of the insertion section.

As illustrated in FIG. 3, an illumination window 31, an observation window 32, and a forceps port 33 are formed in the distal end surface of the tip portion 3c. To wash the distal end surface as required, a nozzle 34 for sending water and air is formed. The illumination window 31, the observation window 32, the forceps port 33, and the nozzle 34 communicate with the main-body operation section 5 through the channels.

Figure 4:
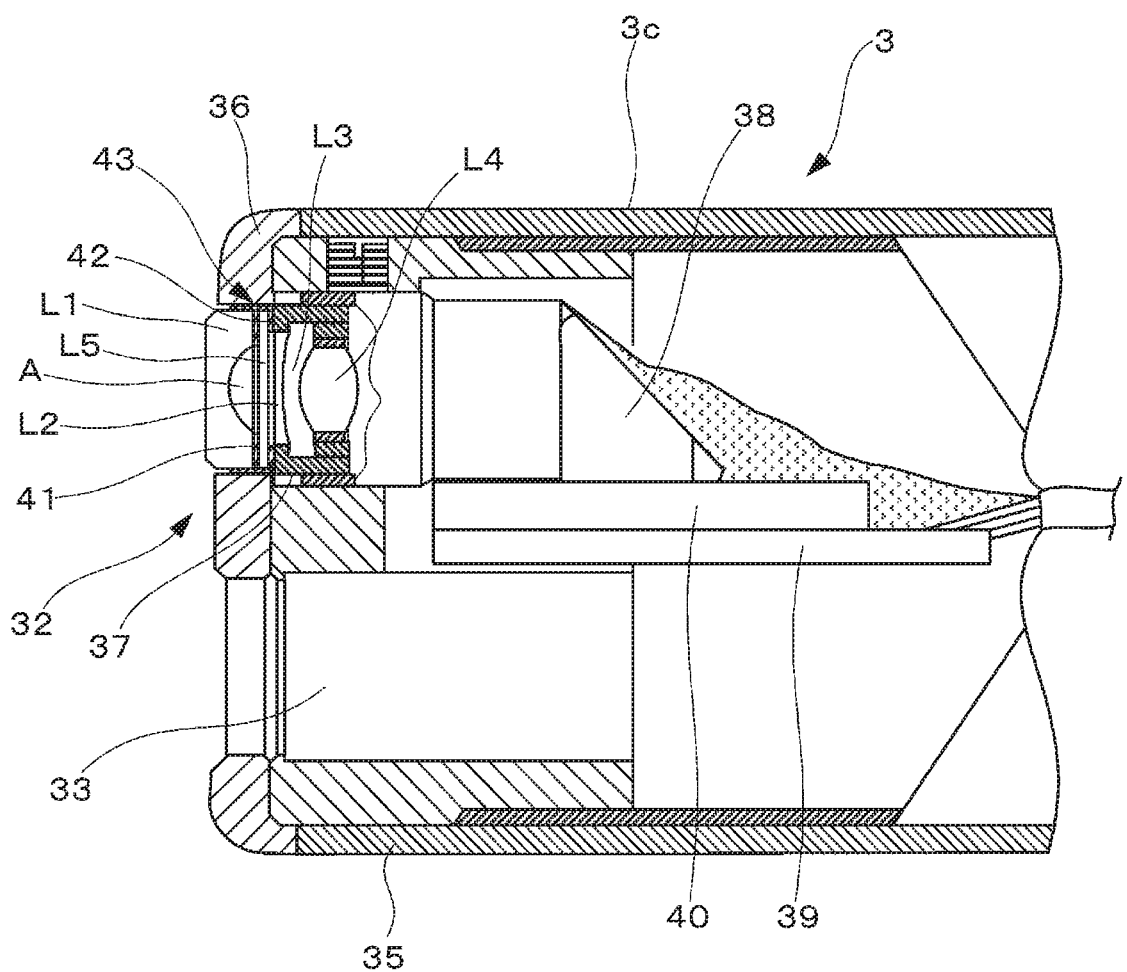
FIG. 4 is a partially cut-away partial sectional view of the tip portion, without hatching that shows sections of lenses and a prism.

As illustrated in FIG. 4, the tip portion 3c is composed of a tip-portion main body 35 made of metal and an end cap 36 made of an electrically insulating material.

An observation unit 43, which is an optical device, is disposed in the observation window 32. The observation unit 43 includes a lens holder 37, and in the lens holder 37, an objective optical system composed of lenses L1 to L5 is fixed with cured adhesives 41 and 42. In the objective optical system, A is an air layer. A prism 38 is bonded and fixed to an end face of the lens holder 37. The optical axis of the objective optical system can be bent at a right angle by the prism 38. The prism 38 is bonded to a solid-state imaging element 40. The solid-state imaging element 40 is fixed to a substrate 39.

Method for Producing Endoscope

A method for producing an endoscope according to the present invention is not particularly limited as long as fixing at least one of a resin member, a metal member, or a glass member by using the adhesive according to the present invention is included. For steps other than fixing of at least one of a resin member, a metal member, or a glass member, usual production steps may be employed to produce the endoscope according to the present invention. For example, the method for producing an endoscope according to the present invention preferably includes a step of mixing the base and the curing agent of the adhesive according to the present invention under reduced pressure, then injecting or applying the adhesive according to the present invention into a target portion, and heating the adhesive at 10° C. to 120° C. (preferably 20° C. to 100° C., more preferably 40° C. to 80° C.) for 0.5 to 24 hours.

Use of Adhesive

The adhesive according to the present invention is used to fix at least one of a resin member, a metal member, or a glass member constituting an insertion section of an endoscope, to another member constituting the endoscope. That is, the fixing is performed by bonding at least one of the resin member, the metal member, or the glass member to a supporting member (e.g., a resin member, a glass member, or a metal member). Preferably, the adhesive according to the present invention is used to fix a resin member to a metal member, to fix a metal member to a resin member, or to fix a metal member to another metal member.

Specific examples of how the adhesive according to the present invention is used will be described below, but the present invention is not limited to these examples.

Examples of resin members include tubes inserted into an insertion section of an endoscope. The tubes include various tubes produced using various materials such as fluorocarbon resins such as Teflon (registered trademark), resins such as polysulfone resins, polyester resins, polyolefin resins, and silicone resins, and rubber. The adhesive according to the present invention can be used, for example, to bond a metal member or a glass member constituting an insertion section of an endoscope to any of the above tubes (to fix the metal member or the glass member to any of the above tubes).

The adhesive according to the present invention can also be used to form the cured adhesive layer 17 in FIG. 2. The adhesive according to the present invention can also be used to bond together the resin layer 15 and the coat layer 16 in FIG. 2.

The adhesive according to the present invention can be used for outer-surface finishing and fixing of an end of a flexible outer cover tube (the resin layer 15) (the end on the distal side (the angle portion 3b side) of the flexible tube 3a). Specifically, the flexible tube 3a and the angle portion 3b are bonded together using the adhesive according to the present invention. A string is tightly wound around a portion of the flexible tube 3a near the adhesive joint, a portion of the angle portion 3b near the adhesive joint, and the adhesive joint to reinforce the bonding. The configuration in which the outermost layer on the distal-side end of the flexible tube 3a and the flexible tube 3a side end of the angle portion 3b is formed of the adhesive according to the present invention reduces the likelihood of raveling of the string and facilitates the insertion of the insertion section into a body cavity. The insertion section thus formed can maintain a bright appearance after sterilization.

The adhesive according to the present invention can be used for at least one of bonding of the tip portion 3c and the angle portion 3b or bonding of the insertion section 3 and the main-body operation section 5. Specifically, the tip portion 3c and the angle portion 3b are bonded together using the adhesive according to the present invention. A string is tightly wound around a portion of the tip portion 3c near the adhesive joint, a portion of the angle portion 3b near the adhesive joint, and the adhesive joint to reinforce the bonding. In the same manner as described above, the adhesive is applied so as to cover the string and cured. The bonding of the insertion section 3 and the main-body operation section 5 is performed in the same manner.

Preferably, the adhesive according to the present invention is used to fix various tubes inserted into the insertion section of the endoscope to at least one of the tip portion 3c or the main-body operation section 5.

The adhesive according to the present invention is preferably used for the tip portion 3c. Among the uses for the tip portion 3c, the adhesive according to the present invention is preferably used to seal the illumination window 31 and the observation window 32 (to fix the glass members). This is because a thick coating of the adhesive according to the present invention can smoothen the outer corners of the lenses and block the entrance of light from the lateral sides of the lenses.

The adhesive according to the present invention can be used to fix at least one of a metal member or a glass member, for example, to assemble the imaging device built in the tip portion 3c, to bond parts together, or to seal the solid-state imaging element 40. The imaging device has an optical system composed of a plurality of optical parts, such as the lenses L1 to L5 and the prism 38, and has the solid-state imaging element 40, such as a charge coupled device (CCD), that photoelectrically converts an optical image formed by the optical system into an imaging signal. The adhesive according to the present invention can be used, for example, to bond together optical parts, such as the lenses L1 to L5 and the prism 38 made of materials such as glass and to bond at least one of the lenses L1 to L5 or the prism 38 to the substrate 39 made of resin or metal. This bonding can fix the glass members and can fix the metal member.

The adhesive according to the present invention can be used for bond-fixing and sealing of the solid-state imaging element 40 and the substrate 39. This bonding can fix the metal members constituting the solid-state imaging element, the substrate, and the like.

EXAMPLES

The present invention will now be described in more detail with reference to examples. These examples should not be construed as limiting the present invention. "Room temperature" means 25° C.

Production of Sheet-Like Cured Product (Example 1)

Using a "THINKY MIXER ARV-310 (trade name, manufactured by THINKY CORPORATION)", 100 parts by mass of an epoxy resin (A-1) (bisphenol A diglycidyl ether ("jER825" (trade name) manufactured by Mitsubishi Chemical Corporation, epoxy equivalent: 170) serving as a base and 5 parts by mass of a tertiary amine compound (B-1) (N,N,N'N'-tetramethyl-1,6-hexanediamine) serving as a curing agent were defoamed for 3 minutes with stirring at 2000 rpm under a reduced pressure of 1.0 Pa at room temperature to obtain a mixture. The mixture was cured at 80° C. for 6 hours with a MINI TEST PRESS (manufactured by Toyo Seiki Seisaku-sho, Ltd.) to obtain a sheet-like cured product 100 mm long×100 mm wide×0.4 mm thick.

Production of Sheet-Like Cured Products (Examples 2 to 16 and Comparative Examples 1 to 4)

Sheet-like cured products of Examples 2 to 16 and Comparative Examples 1 to 4 were produced in the same manner as the sheet-like cured product of Example 1 except that the composition was changed as shown in Table 1 given below.

Hydrogen Peroxide Plasma Resistance Test

Using a STERRAD (registered trademark) NX (trade name, manufactured by Johnson & Johnson) advanced course, a hydrogen peroxide plasma sterilization treatment was performed on the above sheet-like cured products at room temperature. Using a Tensilon universal material testing instrument RTF-1210 (trade name, manufactured by A & D Company. Limited), an elongation tensile test was performed on the sheet-like cured product before the sterilization treatment and the sheet-like cured product subjected to the sterilization treatment 100 times. The change in breaking strength before and after the sterilization treatment was evaluated. In this test, A, B, and, C are acceptable.

Evaluation Criteria

A: The breaking strength was 95% or more of that before a sterilization treatment.

B: The breaking strength was 90% or more and less than 95% of that before a sterilization treatment.

C: The breaking strength was 85% or more and less than 90% of that before a sterilization treatment.

D: The breaking strength was less than 85% of that before a sterilization treatment.

E: The sample was degraded and broken during a hydrogen peroxide plasma sterilization treatment, and a tensile test could not be performed.

[Lesser Decreases Indicate that the Cured Product has Undergone Less Oxidation Degradation.]

Anti-Dripping Properties

Using a "THINKY MIXER ARV-310 (trade name, manufactured by THINKY CORPORATION)", an epoxy resin (A) and an amine compound in amounts shown in Table 1 below were defoamed for 3 minutes with stirring at 2000 rpm at room temperature under a reduced pressure of 1.0 Pa to obtain a mixture. The mixture was applied to an upright polyester sheet (manufactured by AS ONE Corporation) so as to be 1 cm wide, 3 cm long, and 2 mm thick, and dripping in the vertical direction after 10 seconds was evaluated. In this test, A and B are acceptable.

Evaluation Criteria
  A: The dripping length is less than 1 cm.
  B: The dripping length is 1 cm or more and less than 3 cm.
  C: The dripping length is 3 cm or more and less than 5 cm.
  D: The dripping length is 5 cm or more.
[Shorter Dripping Lengths Indicate Higher Suitability for Thick Coating.]

TABLE 1

| | | Example 1 | Example 2 | Example 3 | Example 4 | Example 5 |
|---|---|---|---|---|---|---|
| Epoxy resin (A) | Type | (A-1) | (A-2) | (A-3) | (A-4) | (A-5) |
| | Content [parts by mass] | 100 | 100 | 100 | 100 | 100 |
| Amine compound | Type | (B-1) | (B-1) | (B-1) | (B-1) | (B-1) |
| | Content [parts by mass] | 5 | 5 | 5 | 5 | 5 |
| Percentage [by mass] of tertiary amine compound (B) in curing agent | | 100 | 100 | 100 | 100 | 100 |
| Curing temperature | ° C. | 80 | 80 | 80 | 80 | 80 |
| Curing time | hr | 6 | 6 | 6 | 6 | 6 |
| Hydrogen peroxide plasma resistance | | A | A | A | A | A |
| Suitability for thick coating | | A | A | A | A | A |

| | | Example 6 | Example 7 | Example 8 | Example 9 | Example 10 |
|---|---|---|---|---|---|---|
| Epoxy resin (A) | Type | (A-6) | (A-7) | (A-2) | (A-2) | (A-2) |
| | Content [parts by mass] | 100 | 100 | 100 | 100 | 100 |
| Amine compound | Type | (B-1) | (B-1) | (B-2) | (B-3) | (B-4) |
| | Content [parts by mass] | 5 | 5 | 5 | 5 | 5 |
| Percentage [by mass] of tertiary amine compound (B) in curing agent | | 100 | 100 | 100 | 100 | 100 |
| Curing temperature | ° C. | 80 | 80 | 80 | 80 | 80 |
| Curing time | hr | 6 | 6 | 6 | 6 | 6 |
| Hydrogen peroxide plasma resistance | | A | A | A | A | A |
| Suitability for thick coating | | A | A | B | A | B |

| | | Example 11 | Example 12 | Example 13 | Example 14 | Example 15 |
|---|---|---|---|---|---|---|
| Epoxy resin (A) | Type | (A-2) | (A-2) | (A-2) | (A-2) | (A-3) |
| | Content [parts by mass] | 100 | 100 | 100 | 100 | 100 |
| Amine compound | Type | (B-5) | (B-1) | (B-1) | (B-1) | (B-1), (C-1) |
| | Content [parts by mass] | 5 | 0.3 | 1 | 12 | 4, 1 |
| Percentage [by mass] of tertiary amine compound (B) in curing agent | | 100 | 100 | 100 | 100 | 80 |
| Curing temperature | ° C. | 80 | 80 | 80 | 80 | 80 |

TABLE 1-continued

| | | | | | | |
|---|---|---|---|---|---|---|
| Curing time | hr | 6 | 24 | 12 | 3 | 6 |
| Hydrogen peroxide plasma resistance | | A | C | B | A | A |
| Suitability for thick coating | | A | A | A | B | B |

| | | Example 16 | Comparative Example 1 | Comparative Example 2 | Comparative Example 3 | Comparative Example 4 |
|---|---|---|---|---|---|---|
| Epoxy resin (A) | Type | (A-2) | (A-2) | (A-2) | (A-2) | (A-2) |
| | Content [parts by mass] | 100 | 100 | 100 | 100 | 100 |
| Amine compound | Type | (B-1), (C-1) | (C-1) | (C-1) | (C-2) | (B-1), (C-1) |
| | Content [parts by mass] | 3.5, 1.5 | 19 | 5 | 50 | 2.5, 2.5 |
| Percentage [by mass] of tertiary amine compound (B) in curing agent | | 70 | 0 | 0 | 0 | 50 |
| Curing temperature | °C. | 80 | 80 | 80 | 80 | 80 |
| Curing time | hr | 6 | 6 | 12 | 6 | 6 |
| Hydrogen peroxide plasma resistance | | B | D | D | E | D |
| Suitability for thick coating | | B | D | C | C | D |

Notes of Table

In Example 15, 4 parts by mass of the tertiary amine compound (B) and 1 part by mass of a compound (C-1) given below were used. In Example 16, 3.5 parts by mass of the tertiary amine compound (B) and 1.5 parts by mass of the compound (C-1) were used. In Comparative Example 4, 2.5 parts by mass of the tertiary amine compound (B) and 2.5 parts by mass of the compound (C-1) were used.

Epoxy Compound (A)

(A-1) Bisphenol A diglycidyl ether ("jER825" (trade name) manufactured by Mitsubishi Chemical Corporation, epoxy equivalent: 170)

(A-2) Bisphenol A diglycidyl ether ("jER828" (trade name) manufactured by Mitsubishi Chemical Corporation, epoxy equivalent: 190)

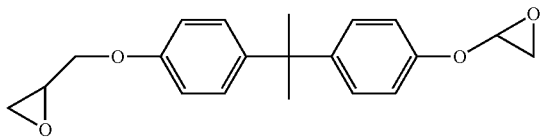

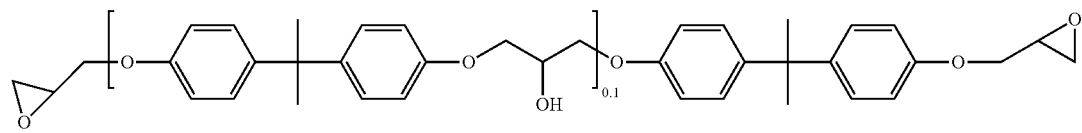

(A-3) Bisphenol A diglycidyl ether ("jER834" (trade name) manufactured by Mitsubishi Chemical Corporation, epoxy equivalent: 230)

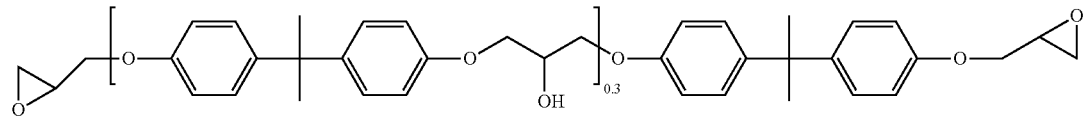

(A-4) Bisphenol F diglycidyl ether ("EPICLON 830" (trade name) manufactured by DIC Corporation, epoxy equivalent: 170)

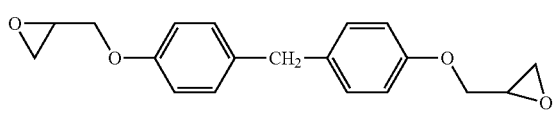

(A-5) Epoxy novolac resin (manufactured by Sigma-Aldrich, product number 406775, epoxy equivalent: 170)

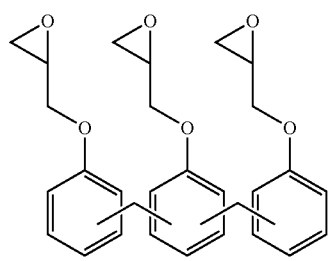

(A-6) Bisphenol A propoxylate diglycidyl ether (manufactured by Sigma-Aldrich, epoxy equivalent: 228)

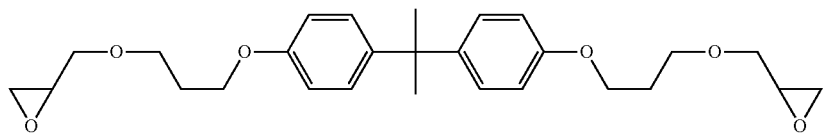 [SMILES: CC(C)(c1ccc(OCCCOCC2CO2)cc1)c1ccc(OCCCOCC2CO2)cc1]

(A-7) 4,4'-Methylenebis(N,N-diglycidylaniline) (manufactured by Tokyo Chemical Industry Co., Ltd., epoxy equivalent: 106)

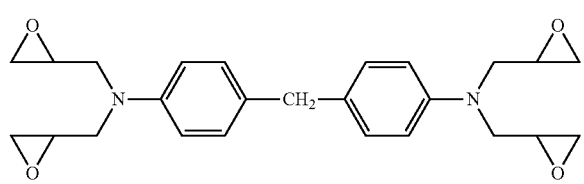 [SMILES: c1cc(N(CC2CO2)CC2CO2)ccc1Cc1ccc(N(CC2CO2)CC2CO2)cc1]

Tertiary Amine Compound (B)

(B-1) N,N,N'N'-Tetramethyl-1,6-hexamethylenediamine (manufactured by Tokyo Chemical Industry Co., Ltd.)

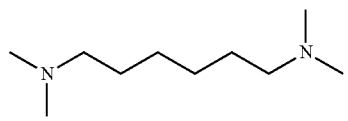

(B-2) N,N'-Dimethylpiperazine (manufactured by Tokyo Chemical Industry Co., Ltd.)

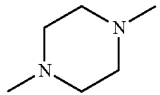

(B-3) 2,4,6-Tris(dimethylaminomethyl)phenol (manufactured by Tokyo Chemical Industry Co., Ltd.)

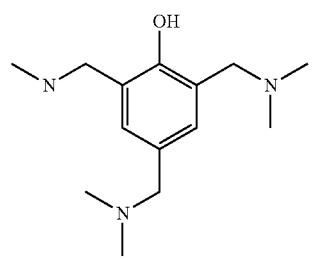

(B-4) 1,8-Diazabicyclo[5.4.0]-7-undecene (manufactured by Tokyo Chemical Industry Co., Ltd.)

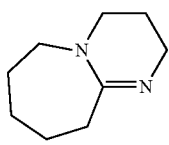 [SMILES: C1CCC2=NCCCN2CC1]

(B-5) 2-Dimethylaminomethylphenol (manufactured by Tokyo Chemical Industry Co., Ltd.)

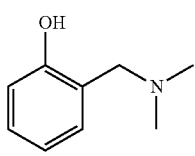

Other Amine Compounds (C-1) m-Xylylenediamine (manufactured by Tokyo Chemical Industry Co., Ltd.)

(C-2) Polyamidoamine curing agent, Hardner HV-953U (trade name, manufactured by Nagase ChemteX Corporation)

In Comparative Examples 1 and 2, the tertiary amine compound (B) was not used as the curing agent, and thus both sterilization resistance and suitability for thick coating were insufficient. In Comparative Example 3, the tertiary amine compound (B) was not used as the curing agent, and the amount of curing agent was large, thus resulting in poor suitability for thick coating and low sterilization resistance. In Comparative Example 4, the tertiary amine compound (B) was used as a part of the curing agent but the percentage of the tertiary amine compound (B) in the curing component was low, and thus both sterilization resistance and suitability for thick coating were insufficient.

By contrast, in Examples 1 to 15 in which the adhesive according to the present invention was used, both sterilization resistance and suitability for thick coating were acceptable. Comparison of Example 3 and Example 15 shows that when the content of the tertiary amine compound (B) in the curing agent is 90 mass % or more, the adhesive according to the present invention has higher suitability for thick coating.

While the present invention has been described in connection with embodiments thereof, we do not intend to limit our invention in any detail of the description unless otherwise specified. Rather, the invention should be broadly construed without departing from the spirit and scope of the invention as defined by the appended claims.

REFERENCE SIGNS LIST 2 electronic endoscope (endoscope)
3 insertion section
　3a flexible tube
　3b angle portion
　3c tip portion
5 main-body operation section
6 universal cord
11 spiral tube
　11a metal strip
12 tubular net
13 cap
14 flexible tube substrate
　14a distal side
　14b proximal side
15 resin layer
16 coat layer
17 cured adhesive layer
31 illumination window
32 observation window
33 forceps port
34 nozzle
35 tip-portion main body
36 end cap
37 lens holder
38 prism
39 substrate
40 solid-state imaging element
41 cured adhesive
42 cured adhesive
43 observation unit
A air layer
L1 to L5 lens

What is claimed is:

1. A method of fixing a constituent member of an endoscope, comprising:
　applying a two-component adhesive to the constituent member of the endoscope and allowing the two-component adhesive to cure,
　the two-component adhesive comprising a base and a curing agent,
　wherein the base includes at least one epoxy resin (A) selected from the group consisting of bisphenol A epoxy resins, bisphenol F epoxy resins, and phenol novolac epoxy resins, and
　the curing agent includes a tertiary amine compound (B), the tertiary amine compound (B) accounting for 60 mass % or more of a curing component included in the curing agent.

2. The method according to claim 1, wherein the tertiary amine compound (B) includes a compound represented by general formula (I):

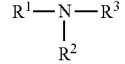

general formula (I)

where $R^1$ to $R^3$ each independently represent an aliphatic hydrocarbon group, an aromatic hydrocarbon group, or an aromatic heterocyclic group.

3. The method according to claim 1, wherein the adhesive is used in the form of a mixture of the base and the curing agent with the tertiary amine compound (B) being present in an amount of 0.5 to 10 parts by mass based on 100 parts by mass of the epoxy resin (A).

4. A cured product formed by the method according to claim 1.

5. An endoscope comprising:
　a cured product formed by curing a two-component adhesive, the two-component adhesive comprising a base and a curing agent,
　wherein the base includes at least one epoxy resin (A) selected from the group consisting of bisphenol A epoxy resins, bisphenol F epoxy resins, and phenol novolac epoxy resins, and
　the curing agent includes a tertiary amine compound (B), the tertiary amine compound (B) accounting for 60 mass % or more of a curing component included in the curing agent,
　wherein the cured product fixes at least one of a resin member, a metal member, or a glass member.

6. A method for producing an endoscope, comprising fixing at least one of a resin member, a metal member, or a glass member by applying a two-component adhesive to the at least one of the resin member, the metal member, or the glass member,
　the two-component adhesive comprising a base and a curing agent,
　wherein the base includes at least one epoxy resin (A) selected from the group consisting of bisphenol A epoxy resins, bisphenol F epoxy resins, and phenol novolac epoxy resins, and
　the curing agent includes a tertiary amine compound (B), the tertiary amine compound (B) accounting for 60 mass % or more of a curing component included in the curing agent.

* * * * *